United States Patent [19]

Adrian

[11] Patent Number: 4,667,056
[45] Date of Patent: May 19, 1987

[54] PROCESS FOR PREPARING HYDRATROPIC ACIDS AND ESTERS THEREOF, FROM PROPIPHENONES

[75] Inventor: Guy P. Adrian, Jardin, France

[73] Assignee: Delalande S.A., Courbevoie, France

[21] Appl. No.: 730,369

[22] Filed: May 3, 1985

[30] Foreign Application Priority Data

May 16, 1984 [FR] France ................................ 84 07544

[51] Int. Cl.$^4$ ............................................ C07C 63/00
[52] U.S. Cl. .................................... 562/492; 562/465; 562/496; 560/102; 560/105; 560/59; 560/55
[58] Field of Search .................... 560/102, 105, 59, 55; 562/465, 492, 496

[56] References Cited

FOREIGN PATENT DOCUMENTS

MFR5737  3/1968  France ................. 562/492
7163337  7/1982  Japan .................... 562/492

Primary Examiner—Paul J. Killos
Attorney, Agent, or Firm—Andrew F. Kehoe

[57] ABSTRACT

A process for preparing hydratropic acids and the esters thereof, of formula Ar—CH(CH$_3$)—COOR where R=H or lower alkyl and Ar=phenyl possibly substituted. This process consists in reacting on the propiophenones of formula ArCOCH$_2$CH$_3$, a chlorinating or brominating agent, an alcohol R'OH where R'=lower alkyl, an orthoester R$_1$—C(OR')$_3$ wherein R$_1$=H or lower alkyl, and metal zinc; then possibly hydrolyzing the esters obtained.

With this process can be prepared hydratropic acids known for their anti-inflammatory activity.

9 Claims, No Drawings

PROCESS FOR PREPARING HYDRATROPIC ACIDS AND ESTERS THEREOF, FROM PROPIPHENONES

The present invention relates to a novel process for preparing hydratropic acids and esters thereof, corresponding to the formula:

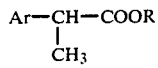 (I)

in which:
R represents a hydrogen atom or a lower alkyl group, and
Ar represents a phenyl nucleus or a phenyl nucleus substituted by at least one group not likely to deactivate the phenyl nucleus.

A process for preparing such compounds has already been described in the European patent application No. 034 871 where it is proposed to operate in three successive steps, namely:

(a) reaction of bromine on a propiophenone of formula:

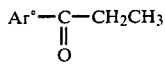

wherein $Ar^o$ is an aryl nucleus, (b) reaction of the resulting bromopropiophenone with an orthoester of formula:

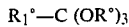

wherein $R_1^o = H$ and $R^o = $ lower alkyl and a primary alcohol of formula:

wherein $R^o = $ lower alkyl (c) transposition of the resulting acetal in the presence of an organic or mineral metal salt.

The main difficulty with this method of synthesis resides in the acetalization step (b) which is an equilibrated reaction requiring an excess of acetalization reagents and extended reflux times for a 70-80 % yield only.

Productivity is therefores low in this step (b) and the method of synthesis proposed in the above document therefore requires to be improved for profitable industrial use.

The applicant has been led to study new methods of synthesis of hydratropic acids (compounds with anti-inflammatory activity) and of the corresponding esters. He has thus discovered that the compounds of formula (I) could be obtained with excellent yields and without excessive consumption of reagents, by reacting on the propiophenones of formula:

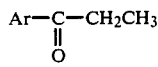 (II)

wherein Ar has the same meaning as in formula (I), a chlorinating or brominating agent, a primary alcohol of formula:

 (III)

wherein R' represents a lower alkyl group, an orthoester of formula:

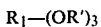 (IV)

wherein $R_1$ represents a hydrogen atom or a lower alkyl group and R' has the same meaning as in formula (III) and metal zinc, preferably in powder form, then by possibly hydrolyzing the resulting esters of formula:

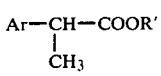 (Ia)

wherein R' has the same meaning as in formula (III) or (IV) so as to obtain the corresponding acids of formula:

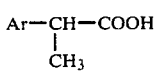 (Ib)

According to the invention, the chlorinating or brominating agent may first of all be caused to react on the propiophenones (II), then cause the alcohol (III), the orthoester (IV) and the metal zinc to react simultaneously on the resulting compounds (chloropropiophenones or bromopropiophenones). Or alternatively, the chlorinating or brominating agent, the alcohol (III), the orthoester (IV) and the metal zinc may be caused to react simultaneously on the propiophenones, which may be accomplished, for example, by adding the chlorinating or brominating agent gradually to the propiophenone (II)/alcohol (III)/orthoester (IV)/metal zinc mixture.

It should be noted that the simultaneous reaction of the chlorinating or brominating agent, the alcohol (III), the orthoester (IV) and the metal zinc on the propiophenones or the simultaneous reaction of the alcohol (III), the orthoester (IV) and the metal zinc on the reaction product of the chlorinating or brominating agent and the propiophenones (II) should be carried out with heating, preferably at a temperature of 80°-130° C. A moderate temperature for example (more particularly up to about 45° C.) may be used first of all then the temperature of the reaction medium raised to the final desired temperature while eliminating, during such temperature rise, the volatile products having a boiling point lower than said final desired temperature.

In the present state of knowledge of the reaction mechanism, it would seem that the propiophenones (II) react first of all with the chlorinating or brominating agent to lead to the corresponding chloro- or bromo-propiophenones which in there turn react with the metal zinc to form organozinc compounds which then develop under heating to the compounds (Ia) according to a process which involves no equilibrated reaction likely to adversely affect the yields of the reaction.

The process of the invention thus allows the desired esters to be obtained, in one or two steps, with yields reaching 95%, with reaction times of the order of 2 to 6 hours only.

According to the invention a brominating agent, which is generally more reactive than a chlorinating agent, will preferably be used. The brominating agent includes for exemple, bromine, bromine-chlorine or trimethylphenylammonium perbromide, bromine being particularly preferred because of its availability, its good reactivity and its boiling point which allows it to be reacted at a relatively high temperature.

The reaction may be carried out, should that be necessary, in the presence of an inert diluent, capable of dissolving the compounds (II), (III) and (IV) and having a boiling point allowing the reaction mixture to be brought to the desired temperature; they may more particularly be halogenated diluents such as tetrachloroethylene, tetrachloroethane or chlorobenzene.

The amount of metal zinc to use is not critical and for obvious reasons of economy and of ease of separation from the final reaction mixture, it will be preferably used in catalytic amounts.

The chlorinating or brominating agent and the orthoester (IV) will be used respectively in an amount of at least one molar equivalent and at least two molar equivalents with respect to the propiophenone (II).

As for the primary alcohol (III), it will be used in an amount of at least one molar equivalent with respect to the propiophenone (II); it is however preferable to use it largely in excess, in which case it will play at the same time the role of diluent.

Hydrolysis of the esters (Ia) may be achieved using conventional techniques for the acid or alkaline hydrolysis of an ester into the corresponding acid, such for example as treating the esters (Ia) with aqueous alkali (more particularly aqueous NaOH) in a solvent (more particularly lower alcohol), followed by acidification.

Among the compounds (I) which may be prepared in accordance with the process of the invention may be mentioned those in which R=H or a normal lower alkyl group such as methyl, ethyl, n-propyl and n-butyl and Ar is chosen from the group comprising:

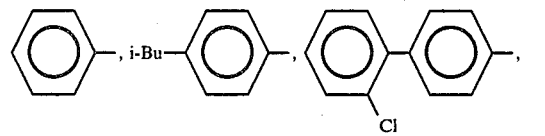

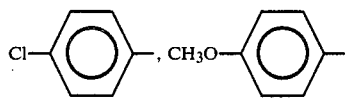

There may be mentioned in particular the compound (I) having the particular structure:

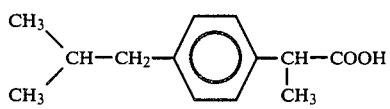

which is ibuprofen, a well known anti-inflammatory agent and the corresponding esters, precursors of ibuprofen.

It should finally be noted that, among the compounds (I), that one with the particular structure:

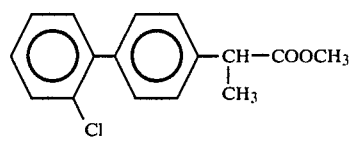

(I'a)

is new; the invention extends consequently to this new compound.

The preparation of some compounds (I) will be given below by way of examples to illustrate the invention.

EXAMPLE 1

Methyl 2-(2'-chloro 4-biphenylyl) propionate

In a 1 liter three-necked flask are charged:
121 g (0.494 mole) of 1-(2'-chloro 4-biphenylyl) propane-1-one
130 g (1.23 mole) of trimethyl orthoformate,
242 ml of methanol, and
2.6 g (0.04 atom-gram) of powdered zinc.

The mixture is heated to 45° C. with stirring and 83 g (0.52 mole) of bromine are added thereto in 20 minutes. The reaction medium becomes straw yellow colored. The medium is heated progressively for 1 hour from 45° C. to 115° C. while distilling off the volatile products between 32° and 65° C. It is kept for 45 minutes between 115° and 120° C., then cooled to 30° C. and 250 ml of water are added. The reaction medium is extracted twice with 100 ml of methylene chloride. The organic phase is concentrated then distilled under vacuum, to obtain 111 g of the expected product.

Yield: 81%

$E_{0.1\ torr}$: 155° C.

Melting point: 63° C. (white cristals)

IR Spectrum (KBr): $\nu C{=}O$ 1740 cm$^{-1}$

NMR spectrum (CDCl$_3$)δppm: 1.6 (d, 3H, J=7 CH$_3$); 3.7 (s, 3H, OCH$_3$); 3.8 (q, 1H, J=7 Hz, CH); 7.3-7.7 (m, 8 aromatic Hs).

EXAMPLE 2

Ethyl 2-phenyl propionate

In a 0.5 liter three-necked flask are charged:
26.8 g (0.2 mole) of propiophenone,
74 g (0.5 mole) of triethyl orthoformate,
60 ml of ethanol, and
0.43 g (0.016 atom-gram) of powdered zinc.

33.5 g (0.21 mole) of bromine are added at 45° C. and in 20 minutes, then the volatile products are distilled off between 30° and 80° C. by heating the medium from 45° to 120° C. This latter temperature is maintained for 1 hour. The medium is then diluted with 100 ml of toluene, then washed with 250 ml of water. By distillation 30 g of the expected compound are isolated.

Yield: 84%

$E_{10\ torrs}$: 95° C.

$n_D^{20}$: 1.5025 (in agreement with literature)

Purity: 98%

EXAMPLE 3

Methyl 2-(4-isobutyl phenyl) propionate

In a 1 liter reactor are charged:
190.3 g (1 mole) of para-isobutylpropiophenone,
220 g (2.08 moles) of trimethyl orthoformate,
380 ml of methanol, and
5.2 g (0.08 atom-gram) of powdered zinc The mixture is heated to 45° C. with stirring and 162 g (1.013 mole) of bromine are added in 20 minutes. The medium is gradually heated from 45° C. to 115° C. in 1 hour, while distilling between 32 and 65° C. It is maintained at 115° C. for 1 hour, cooled to 30° C., 500 ml of water are added, and it is extracted twice with 200 ml of methylene chloride. The organic phase is concentrated and distilled under vacuum. Thus, 197 g of the expect product are isolated.

Yield: 89%
$E_{0.1 \, torr}$: 95° C.
GLC titer: 99.5%

EXAMPLE 4

2-(4-isobutyl phenyl) propionic acid or ibuprofen

In a 6 liter reactor are charged.
749 g (3.95 moles) of para-isobutylpropiophenone,
951 g (8.96 moles) of trimethyl orthoformate,
1500 ml of methanol,
20.9 g (0.32 atom-gram) of powdered zinc, and
750 ml of tetrachloroethylene used as diluent.

The mixture is heated to 40° C. with agitation and 656 g (4.1 moles) of bromine are added in 1 hour. The mixture is maintained for 30 minutes at 45° C. then 2 liters of products having a boiling point between 34° and 62° C. are distilled off, the internal temperature being between 45° and 85° C. At this stage, 750 ml of tetrachloroethylene are added and the mixture is heated to 100° C. Vigorous boiling occurs and the internal temperature is stabilized at 128° C. After 1 hour, it is cooled to 75° C. and 2 liters of water are added. It is decanted and the organic phase is concentrated at 80° C. under 20 torrs to recover 1400 ml of tetrachloroethylene and 886 g of a residue formed mainly of methyl 2-para-isobutylphenyl propionate. Thiw raw product is dissolved in 2.25 liters of methanol mixed with 400 g (10 moles) of NaOH and 2.5 liters of water. It is brought to reflux for 2 hours, the methanol is distilled off until an internal temperature of 95° C. is reached, collecting 2.5 liters of a methanol-water mixture. It is left for 6 hours to cristalize and the sodium salt formed is filtered. It is washed on the filter with 1 liter of tetrachloroethylene and redissolved in 2 liters of water. The solution obtained is acidified to pH 2 with 390 ml of 36% hydrochloric acid, left to cristallise at 15° C., the precipitate formed is filtered, this latter is dried at 50° C., which leads to 670 g (yield: 81%) of the expected product (melting point 76° C.).

I claim:

1. A process for preparing hydratropic acids and the esters thereof, corresponding to the formula:

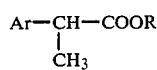  (I)

in which:
R represents a hydrogen atom or a lower alkyl group, and
Ar represents a phenyl nucleus or a phenyl nucleus substituted by at least one group not likely to deactivate the phenyl nucleus, characterized in that it consists in reacting on the propiophenones of formula:

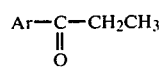  (II)

wherein Ar has the same meaning as in formula (I), a chlorinating or brominating agent, a primary alcohol of formula:

R'—OH  (III)

wherein R' represents a lower alkyl group, an orthoester of formula:

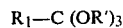  (IV)

wherein $R_1$ represents a hydrogen atom or a lower alkyl group and R' has the same meaning as in formula (III) and metal zinc, then possibly hydrolyzing the resulting ester of formula:

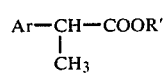  (Ia)

wherein R' has the same meaning as in formula (III) or (IV), to obtain the corresponding acids of formula:

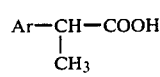  (Ib)

2. The process as claimed in claim 1, characterized in that it consists in reacting the chlorinating or brominating agent on the propiophenones (II), then in reacting on the resulting compounds simultaneously the alcohol (III), the orthoester (IV) and the metal zinc.

3. The process as claimed in claim 1, characterized in that it consists in reacting simultaneously on the propiophenones (II), the chlorinating or brominating agent, the alcohol (II), the orthoester (IV) and the metal zinc.

4. The process as claimed in claim 1, 2 or 3, characterized in that the simultaneous reaction of the chlorinating or brominating agent, of the alcohol (III), of the orthoester (IV) and of the metal zinc on the propiophenones (II) or the simultaneous reaction of the alcohol (III), of the orthoester (IV) and of the metal zinc on the reaction product of the chlorinating or brominating agent and the propiophenones is carried out under heating.

5. The process as claimed in claim 4, characterized in that the reaction is carried out at 80°–130° C.

6. The process as claimed in any one of claims 1, 2 or 3 in which a brominating agent is used, characterized in that this latter is bromine.

7. The process as claimed in any one of claims 1, 2 or 3, characterized in that the metal zinc is used in a catalytic amount.

8. The process as claimed in any one of claims 1, 2 or 3, characterized in that the chlorinating or brominating agent and the orthoester (IV) are used respectively in an amount of a molar equivalent and two molar equivalents with respect to the propiophenones (II), the alcohol (III) being used in an amount of at least one equivalent with respect to the propiophenones (II).

9. The process as claimed in any one of claims 1, 2 or 3, characterized in that in the formulae (I) to (IV), R and R' represent a normal lower alkyl group and Ar a
group chosen from the following:
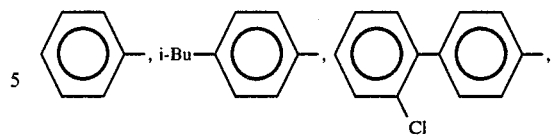
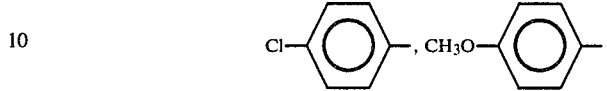
* * * * *

UNITED STATES PATENT AND TRADEMARK OFFICE
CERTIFICATE OF CORRECTION

PATENT NO. : 4,667,056
DATED : 19 May 1987
INVENTOR(S) : Guy P. Adrian

It is certified that error appears in the above—identified patent and that said Letters Patent is hereby corrected as shown below:

Column 4, Line 38    NMR spectrum $(CDCl_3)$ $\delta$ ppm:1.6(d,3H,J=7CH$_3$)

should read

NMR spectrum $(CDCl_3)$ $\delta$ ppm:1.6(d,3H,J=7Hz,CH$_3$)

Signed and Sealed this

Twenty-ninth Day of September, 1987

Attest:

DONALD J. QUIGG

Attesting Officer    Commissioner of Patents and Trademarks